United States Patent [19]
Takahashi et al.

[11] Patent Number: 5,827,172
[45] Date of Patent: Oct. 27, 1998

[54] OPTICAL SYSTEM FOR ELECTRONIC ENDOSCOPES

[75] Inventors: Kazuaki Takahashi; Yuichi Torii, both of Omiya, Japan

[73] Assignee: Fuji Photo Optical Co., Ltd., Omiya, Japan

[21] Appl. No.: 931,769

[22] Filed: Sep. 16, 1997

[30] Foreign Application Priority Data

Sep. 30, 1996 [JP] Japan .................................. 8-280187

[51] Int. Cl.⁶ ............................................... A61B 1/04
[52] U.S. Cl. ........................ 600/176; 600/174; 600/177; 600/182
[58] Field of Search .................................. 600/109, 129, 600/130, 160, 171, 174, 175, 176, 177, 178, 182; 348/340; 359/640, 367

[56] References Cited

U.S. PATENT DOCUMENTS

| | | | |
|---|---|---|---|
| 3,548,808 | 12/1970 | Takahashi et al. ...................... | 600/176 |
| 3,901,220 | 8/1975 | Koyasu et al. ........................... | 600/176 |
| 4,500,181 | 2/1985 | Takashi .................................... | 600/177 |
| 4,660,982 | 4/1987 | Okada ..................................... | 600/175 |
| 4,720,178 | 1/1988 | Nishioka et al. ........................ | 600/175 |
| 4,761,630 | 8/1988 | Takahashi ............................... | 600/177 |
| 4,856,495 | 8/1989 | Tohjoh et al. ........................... | 600/175 |
| 4,919,114 | 4/1990 | Miyazaki ................................. | 600/175 |
| 4,941,457 | 7/1990 | Hasegawa ............................... | 600/175 |
| 5,411,020 | 5/1995 | Ito ............................................ | 600/177 |
| 5,584,793 | 12/1996 | Sauer et al. ............................. | 600/175 |
| 5,704,896 | 1/1998 | Fukunishi et al. ...................... | 600/109 |
| 5,711,756 | 1/1998 | Chikama .................................. | 600/175 |
| 5,749,827 | 5/1998 | Minami ................................... | 600/109 |

*Primary Examiner*—Gene Mancene
*Assistant Examiner*—Ira Hatton
*Attorney, Agent, or Firm*—Ronald R. Snider

[57] ABSTRACT

An optical system for electronic endoscopes which makes it possible to thin tips of endoscopes and minimize illumination ununiformities. In this optical system, a prism having a half transmissive mirror film formed thereon is disposed on a rear side of an objective optical system, a CCD is optically connected to a reflecting optical path in which rays are flexed at a right angle and a light guide is connected to a straight travelling optical path. A light diffusing plate and a condenser lens are arranged between the light guide and the prism. This arrangement makes it possible to dispose the objective optical system in series with the light guide in a tip of endoscope, thereby enabling to thin the tip. Further, the diffusing plate prevents an image of a shape of an end surface of an optical fiber bundle from being projected reversely to an image pickup device. Furthermore, insufficient amount of rays in an outer circumferential portion can be corrected and uniform illumination can be obtained by arranging optical fibers at a higher density in an outer circumferential portion of the light guide.

5 Claims, 3 Drawing Sheets

OPTICAL SYSTEM FOR ELECTRONIC ENDOSCOPES

BACKGROUND OF THE INVENTION

This application claims the priority of Japanese Patent Application No. 8-280187 filed on Sep. 30, 1996, which is incorporated herein by reference.

FIELD OF THE INVENTION

The prevent invention relates to an optical system for electronic endoscopes, and more specifically a configuration of optical members which is used for illuminating interiors of objects to be observed by way of a light guide and observing images of the interiors of the objects picked up by an image pickup device by way of an objective optical system.

DESCRIPTION OF THE PRIOR ART

An electronic endoscope illuminates an interior of an object to be observed with rays transmitted from a tip thereof by way of light guides consisting of optical fiber bundles and picks up, with an image pickup device, an image of the object to be observed which is captured by an objective optical system. In such an electronic endoscope, two light guides are disposed, for example, to a leading end surface, and the objective optical system is disposed between the two light guides so that an image of an illuminated interior of an object to be observed is favorably picked up.

Since the tip of the electronic endoscope described above is inserted into a location to be observed such as a thin body cavity, it is demanded to thin the tip (an insert section), and it is practiced to thin also the light guides described above and contrive their dispositions. For favorable observation, however, it is necessary to obtain a bright illumination light beam and not advantageous to thin the light guides excessively.

Further, such an endoscope poses a problem that it is relatively difficult to unevenly or uniformly illuminate a location whose image is to be captured by the objective optical system. In other words, when two light guides are used as described above, light beams from these light guides are overlapped with each other at a predetermined location, thereby producing illumination ununiformities at a marginal portion of the location. When a single light guide is used, a light beam falls, strictly speaking, obliquely on a location to be irradiated, thereby producing illumination ununiformities similarly at a marginal portion of this location.

SUMMARY OF THE INVENTION

The present invention which has been achieved in view of the problems described above has a primary object to provide an optical system for electronic endoscopes which enables to thin tips of electronic endoscopes and eliminate illumination ununiformities as far as possible.

For accomplishing the object described above, the optical system for electronic endoscopes according to the present invention is characterized in that it comprises an objective optical system which captures an image of an object to be observed, an optical path coupling optical element which is disposed on a rear side of the objective optical system, and forms a reflecting optical path in which rays in a direction along an optical axis of the objective optical system are flexed nearly at a right angle and a straight travelling optical path in which rays in the direction along the optical axis of the objective optical system travel straight, an image pickup device which is optically connected to either one of the reflecting optical path and the straight travelling optical path formed by the optical path coupling optical element, and a light guide which is optically connected to the other optical path and consists of an optical fibers.

Usable as the optical path coupling optical element is a right angle prism which has a half transmissive mirror film formed on a slant surface thereof.

In the configuration described above, rays which are emitted from a light source and emerge from the light guide are led into the objective optical system by way of the optical path coupling optical element and illumination rays are transmitted from the objective optical system to the object to be observed. On the other hand, an image of an interior of the object to be observed is captured by the objective optical system and imaged rays are sent to the image pickup device by way of the optical path coupling optical element and imaged on an image pickup surface of the image pickup device. In such a configuration, the objective optical system and the light guide are disposed concentrically in a tip of the endoscope, thereby providing a merit to allow an attempt to be made to thin the tip.

Further, it is preferable to dispose a diffusing plate for diffusing rays between the light guide and the optical path coupling optical element. This diffusing plate prevents an image of an end surface shape of the light guide consisting of multiple bound optical fibers from being projected reversely to the image pickup device.

Furthermore, in the light guide described above, it is possible to arrange optical fibers so as to be denser on a side of an outer circumference than on a side of a center. When the optical fibers are disposed as described above, a light amount is larger on the side of the outer circumference than on the side of the center, thereby making it possible to perform uniform illumination by solving the problem of insufficient light amount on the side of the outer circumference. In other words, an inconvenience that the outer circumference is rather darker is produced as described above even when a uniform and efficient illuminated condition is obtained by coinciding an illuminated region with an observed region. Therefore, the present invention is configured to obtain a uniformly illuminated condition by increasing a light amount in an outer circumferential portion.

DESCRIPTION OF THE PREFERRED EMBODIMENT

Figure 1:
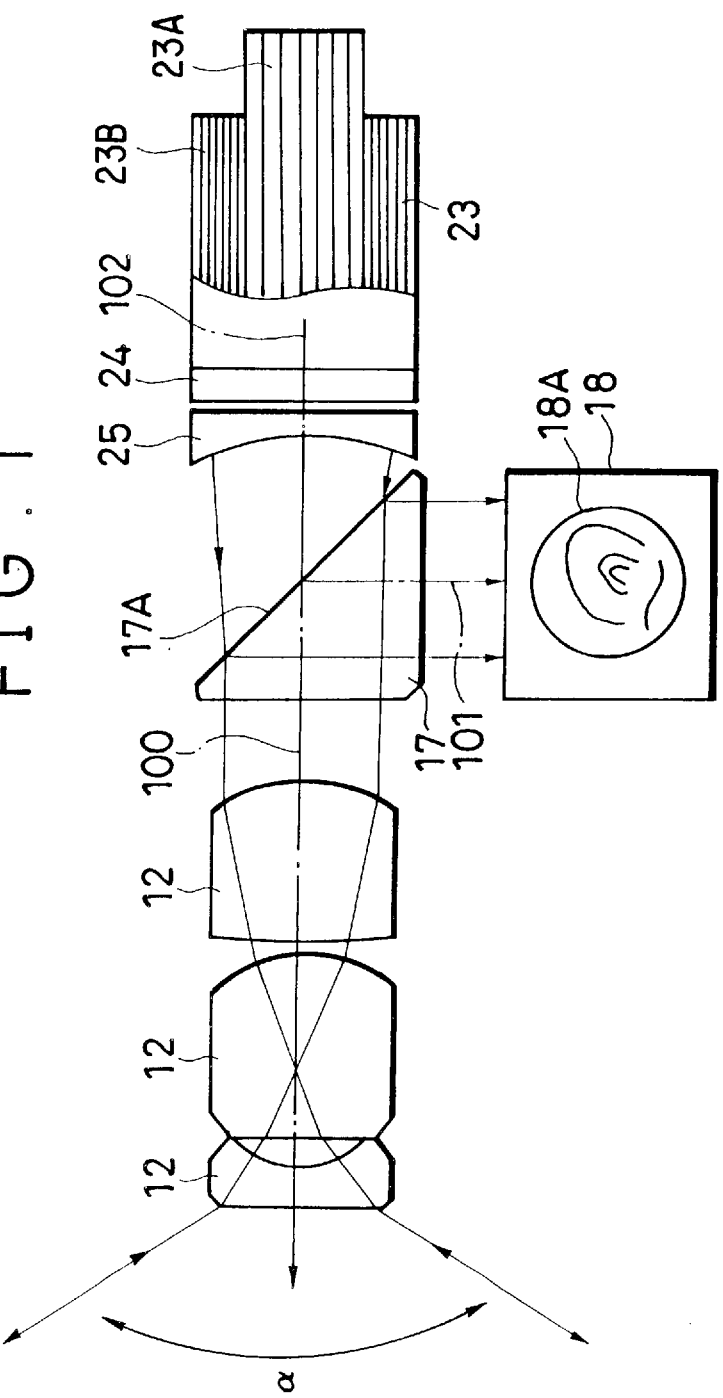
FIG. 1 is a sectional view descriptive of a configuration of an embodiment of the optical system for electronic endoscopes according to the present invention.
Figure 2:
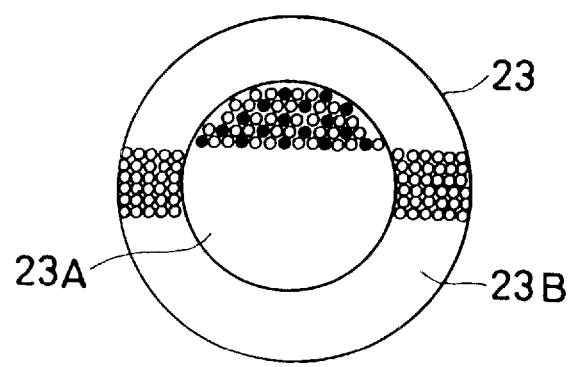
FIG. 2 is a diagram descriptive of arrangement of optical fibers on an end surface of a light guide shown in FIG. 1.
Figure 3:
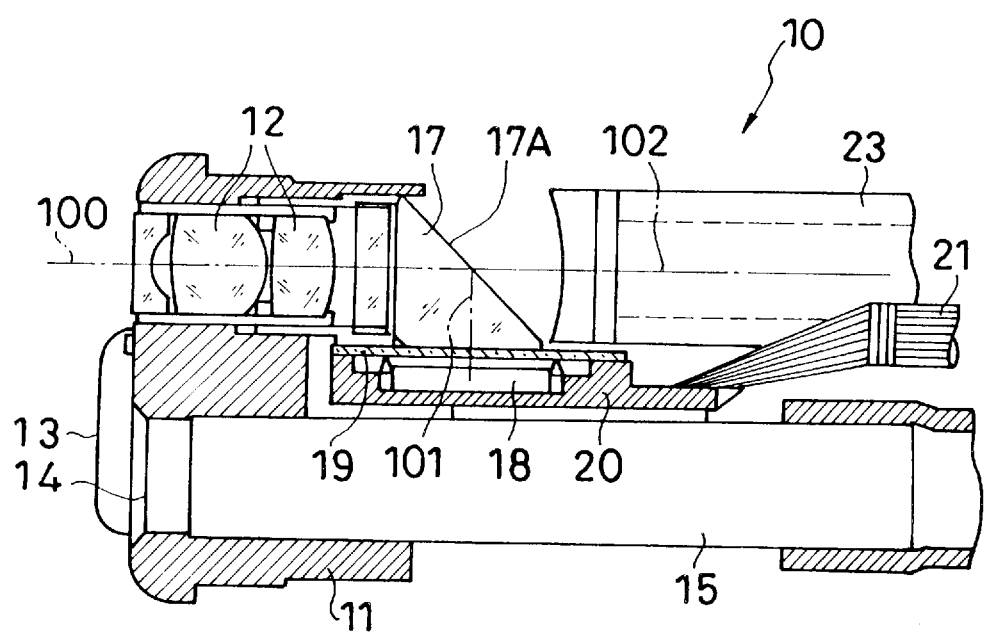
FIG. 3 is a side sectional view illustrating configuration of a tip of the electronic endoscope in an embodiment of the present invention.
Figure 4:
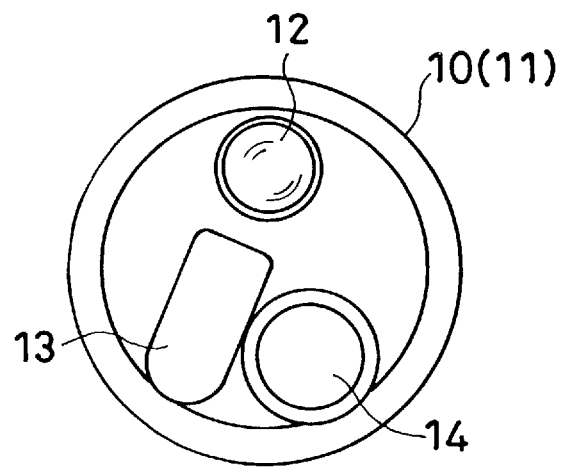
FIG. 4 is a sectional view illustrating a leading end surface of the tip shown in FIG. 3.
Figure 5:
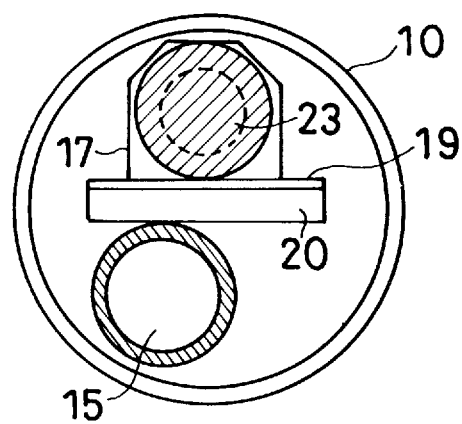
FIG. 5 is a rear view of the tip shown in FIG. 3.

An embodiment of the optical system for electronic endoscopes according to the present invention is shown in FIGS. 1 and 2, whereas a configuration of a tip of an electronic endoscope is illustrated in FIGS. 3 through 5. In FIG. 3 first, objective optical system members (endoscope tube) 12 are disposed in a tip 10 in a condition where they are held by a holder member 11. This objective optical system member 12 includes not only an objective lens but also a stop, a filter and so on. An air feed/water feed nozzle 13 and a forceps port 14 are disposed in a leading end surface of the tip 10 as shown in FIG. 4, and the air feed/water feed nozzle 13 is used for feeding air and washing water to an observation window of the objective optical system members 12.

The forceps port 14 is connected to a treating tool insertion channel 15 shown in FIG. 3 so that various types of treating tools such as forceps can be led out of the forceps port 14 by way of the treating tool insertion channel 15.

In FIG. 3, a right angle prism 17 is optically connected as an optical path coupling optical element to a rear side of the objective optical system members 12 and a CCD 18 as an image pickup device is optically connected to a lower side of the prism 17. The CCD 18 is accommodated and connected in a CCD package 20 which is tightly enclosed with a cover glass plate 19, which is cemented to a bottom surface of the prism 17. A wiring pattern is formed on the CCD package 20 and a signal line 21 for external connection is connected by way of the wiring pattern.

A light guide 23 is disposed on a rear side of the prism 17 and a light source beam emitted from a light source is incident from the light guide 23 onto the prism 17. A half transmissive mirror film 17A is formed on a rear surface (slant surface) of the prism 17 as shown in FIG. 1, thereby forming a reflecting optical path (optical axis 101) which reflects rays from the objective optical system members 12 (optical axis 100) at a right angle toward the CCD 18 and a straight travelling optical path (optical axis 102) through which rays pass from the rear surface of the prism 17 to the objective optical system members 12.

Further, a diffusing plate 24 and a condenser lens 25 are disposed between a front side of the light guide 23 and the rear surface of the prism 17: the diffusing plate 24 having a surface which is formed like that of a ground glass plate (matted glass plate) so that an image of a shape of the fiber bundle on an end surface of the light guide 23 will not be projected reversely to the CCD 18. The condenser lens 25 is disposed for allowing the light source beam to be led into an optical path which is the same as an observation optical path formed by the objective optical system members 12. The optical axis 102 of the light guide 23, the diffusing plate 24 and the condenser lens 25 is disposed so as to be aligned with the optical axis 100 of the objective optical system members 12.

Further, the light guide 23 used in the embodiment is contrived so that optical fibers are arranged at a higher density in an outer circumferential portion thereof as shown in FIG. 2. In other words, the optical fiber bundle which composes the light guide 23 is divided into a central region 23A and an outer circumferential region 23B, and dummy lines (linear materials which are not optical fibers, broken and ineffective optical fibers or the like) which are represented by black spots are disposed among optical fibers designated by white spots in the central region 23A, whereas only optical fibers represented by white spots are arranged in the outer circumferential region 23B. Arrangement density may be varied by selecting other arrangement modes, for example, a loose arrangement of optical fibers with gaps for the central region 23A and a tightly bound arrangement for the outer circumferential region 23B.

A brief description will be made below of the embodiment of the present invention which has the configuration described above. The objective optical system members 12 described above provide an angle of view α (for example 120 degrees) with the optical path formed therein as shown in FIG. 1. Rays which are led from the light source through the light guide 23 pass through the diffusing plate 24 and are condensed by the condenser lens 25, and only a predetermined amount of rays are allowed to pass through the half transmissive mirror film 17A on the rear surface of the prism 17 and be incident onto the objective optical system members 12 (102→100). Accordingly, this amount of rays pass through the optical path formed in the objective optical system members 12 and are allowed to emerge as illumination rays within a range which is the same as the angle of view α described above, thereby providing an optimum illumination pattern.

On the other hand, an image of an interior of an object to be observed which is illuminated is captured by the objective optical system members 12 at the angle of view α, and imaged rays are led to the prism 17 through an optical path which is the same as that for the illumination rays and a predetermined amount of the imaged rays are reflected at a right angle by the prism 17 (the half transmissive mirror film 17A) (100→101). Accordingly, the image of the interior of the object to be observed is formed on an image pickup surface 18A of the image pickup device 18 as shown in FIG. 1.

In the illumination and image pickup described above, the diffusing plate 24 functions, with its diffusing surface to prevent an image of the shape of the optical fiber bundle on the end surface of the light guide 23 from being projected reversely to the image pickup surface 18A. Further, since the optical fibers are arranged at the higher density in the outer circumferential region 23B of the light guide 23 as already described with reference to FIG. 2, an amount of rays emerging from the outer circumferential portion is larger than that of rays emerging from the central portion, thereby preventing an amount of illumination rays from being insufficient in the outer circumferential portion. In other words, the outer circumferential portion is liable to be darkened due to characteristics of a lens such as spreading of rays when an object to be observed which is a little distant is illuminated, but it is possible to irradiate the object as a whole with uniform rays by enhancing an arrangement density in accordance with the darkening liability.

Furthermore, the embodiment described above wherein the objective optical system members 12 are disposed not in parallel but in series with the light guide 23 in the tip 10 provides a merit that it eliminates the conventional necessity for a space for arranging a light guide, thereby making it possible to thin the tip 10.

Though the CCD 18 is disposed under the prism 17 and the light guide 23 is disposed on the rear side of the prism 17 in the embodiment described above, it is possible to reverse this positional relationship, or the light guide 23 may be disposed under the prism 17 and the CCD 18 may be disposed on the rear side of the prism 17.

As understood from the foregoing description, the optical system for electronic endoscopes according to the present invention, wherein the optical path coupling optical element which is treated so as to be half transmissive is disposed on the rear side of the objective optical system and the observation optical path for this objective optical system is used also as an optical path for illumination rays, permits disposing the objective optical system in series with the light guide, thereby making it possible to thin tips of electronic endoscopes.

What is claimed is:

1. An optical system for electronic endoscopes comprising:

an objective optical system for capturing an image of an object to be observed;

an optical path coupling optical element disposed on a rear side of said objective optical system and treated so as to be half transmissive for forming a reflecting optical path in which rays in a direction along an optical axis of said objective optical system are flexed nearly at a right angle and a straight travelling optical path through which rays in the direction along the optical axis of said objective optical system travel straight;

an image pickup device optically connected to either one of the reflecting optical path and the straight travelling optical path formed by said optical path coupling optical element; and a light guide which is optically connected to the other optical path and composed of optical fibers.

2. An optical system for electronic endoscopes according to claim 1 wherein a right angle prism is used as said optical path coupling optical element and a half transmissive film is formed on a slant surface of this right angle prism.

3. An optical system for electronic endoscopes according to claim 1 wherein a diffusing plate for diffusing rays is disposed between said light guide and said optical path coupling optical element.

4. An optical system for electronic endoscopes according to claim 1 wherein optical fibers are arranged at a higher density on a side of an outer circumference than that on a side of a center of the light guide.

5. An optical system for electronic endoscopes comprising:

an objective optical system for capturing an image of an object to be observed;

an optical path coupling optical element disposed on a rear side of said objective optical system and treated so as to be half transmissive for forming a reflecting optical path in which rays in a direction along an optical axis of said objective optical system are flexed at a right angle and a straight travelling optical path through which rays in the direction along the optical axis of said objective optical system travel straight;

an image pickup device which is optically connected to either one of said reflecting optical path and said straight travelling optical path formed by said optical path coupling optical element;

a light guide which is optically connected to the other optical path and composed of optical fibers; and a diffusing plate which is disposed between said light guide and said optical path coupling optical element, and serves for diffusing rays.

* * * * *